(12) United States Patent
Matsuo (10) Patent No.: US 7,313,946 B2
(45) Date of Patent: Jan. 1, 2008

(54) MOISTURE DETECTOR

(75) Inventor: Yoshiro Matsuo, Tokyo (JP)

(73) Assignee: Matsuo Electric Co., Ltd., Tokyo (JP)

( * ) Notice: Subject to any disclaimer, the term of this patent is extended or adjusted under 35 U.S.C. 154(b) by 0 days.

(21) Appl. No.: 10/892,564

(22) Filed: Jul. 15, 2004

(65) Prior Publication Data

US 2006/0010967 A1   Jan. 19, 2006

(51) Int. Cl.
G01N 25/64   (2006.01)
(52) U.S. Cl. .......................................................... 73/75
(58) Field of Classification Search ................ 73/73, 73/75, 335.02
See application file for complete search history.

(56) References Cited

U.S. PATENT DOCUMENTS

| 2,718,141 | A |   | 9/1955  | Richards |
| 3,575,641 | A | * | 4/1971  | Long et al. ................. 361/178 |
| 3,961,753 | A | * | 6/1976  | Sears ........................... 239/64 |
| 4,774,831 | A | * | 10/1988 | Nordin ........................... 73/75 |
| 4,893,506 | A | * | 1/1990  | Shyu et al. .............. 73/170.19 |
| 4,893,508 | A | * | 1/1990  | Friedman ................. 73/335.02 |
| 5,257,532 | A |   | 11/1993 | Hayakawa et al. |
| 5,287,734 | A | * | 2/1994  | Cuming .......................... 73/75 |

FOREIGN PATENT DOCUMENTS

| JP | 08-103759    |   | 4/1996  |
| JP | 2000-288514  | A | 10/2000 |
| JP | 2002-346526  |   | 2/2002  |
| JP | 2002-286666  |   | 10/2002 |

OTHER PUBLICATIONS

Japanese Office Action mailed Feb. 7, 2007 in corresponding Japanese Patent Application No. 2003-078839 and English translation thereof.

* cited by examiner

Primary Examiner—Hezron Williams
Assistant Examiner—Paul M West
(74) Attorney, Agent, or Firm—Frishauf, Holtz, Goodman & Chick, P.C (57) ABSTRACT

A moisture detector of closed case type according to a heat capacity method is realized by a relatively simple constitution. The moisture detector includes a first temperature sensor for sensing temperature of a detection target; a second temperature sensor for sensing the temperature of the detection target; a small heater for heating the second temperature sensor; and a processing unit for obtaining information relating to moisture percentage in the detection target on the basis of a signal outputted from the first temperature sensor and a signal outputted from the second temperature sensor heated by the small heater.

5 Claims, 6 Drawing Sheets

MOISTURE DETECTOR

BACKGROUND OF THE INVENTION

1. Field of the Present Invention

The present invention relates to a moisture detector for detecting moisture percentage in a detection target that may contain moisture, for example, garbage or soil, and further, to a moisture detector to be used for detecting the start of a rainfall so as to prevent unnecessary watering during the rainfall or protect laundry, agricultural harvest, etc. against rain to maintain their dry condition.

2. Description of a Related Art

As a method of disposal of garbage, there is a method of decomposition disposal utilizing aerobic bacteria for fermentation of the garbage. In such disposal method, for easy activation of the aerobic bacteria, ideas are required for controlling the temperature, the amount of oxygen, moisture and so on in the garbage in accordance with the properties of the aerobic bacteria.

Japanese Patent Application Publication JP-A-2000-288514 discloses a garbage disposer for disposing of garbage by utilizing bacteria. In this garbage disposer, garbage is charged from the garbage charge opening, agitation blades are rotated by a motor, and the garbage is agitated by the agitation blades. Here, for easy activation of the aerobic bacteria, the garbage is heated by a heater. The heat temperature is detected by a temperature sensor so as to be proper heat temperature. However, the garbage disposer include no moisture detector for detecting the moisture percentage in the garbage, and therefore, the garbage disposal under the environment in which moisture exists to such an extent that bacteria are easily activated is not considered.

The environment in which the aerobic bacteria activate and proliferate best is an environment in which the moisture percentage is, for example, 60%. If the moisture percentage is less or more than that, there arise not only the problem of taking long time for the composition disposal of garbage, but also a problem of giving out an abnormal odor or the like. Furthermore, when the garbage is too much dried, there arises a problem that the fine powder of the bacteria bed flies, and thereby, clogging occurs in the piping line or deodorizing line.

By the way, since the garbage discharged from cooking places contains considerable moisture, when new garbage is charged into the garbage disposer, the moisture percentage within the garbage disposer rises to nearly 100%. Afterwards, the moisture percentage within the garbage disposer is gradually reduced and, after the condition in which the moisture percentage becomes optimum lasts in a relatively short period, led to the dry condition. Since such cycle is repeated in the conventional garbage disposer, it can be hardly say that the condition in which the aerobic bacteria are activated easily is created stably.

Generally, as a method of detecting moisture percentage or humidity, there are an electric resistance method, a heat capacity method, an electric capacity method, an optical method, etc., each of which has advantages and disadvantages. As a representative one of those, the electric resistance method suitable for detecting humidity in the air can be cited. When a detector is used in a relatively clear atmosphere as in the weather observation, an open case type detector according to the electric resistance method, that is not enclosed in a closed case, may be sufficient.

However, in order to detect the moisture percentage in the dirt such as garbage, the open case type detector is inappropriate, but a closed case type detector that is enclosed within the closed case is appropriate.

Further, in the case of trying to detect the raindrop hits as in a rainfall detector, the open case type detector is also inappropriate. The reason is as follows. When the raindrops drop on the dirt and dust which have been accumulated on the detector due to a spell of fine weather, the function as a sensor for indicating the sensing results on the basis of changes in the resistance value for moment to moment is lost because the dirt and dust stick to the sensor, and therefore, cleaning is required. Thus, for the rainfall detector, the closed case type detector is also appropriate.

Generally, if the moisture percentage is low in the detection target as in the case of detecting the moisture percentage in the air, the open case type detector can be used, however, if the moisture percentage is high in the detection target, the closed case type detector is appropriate. Accordingly, how to realize a closed case type moisture detector according to the heat capacity method and having a relatively simple constitution becomes a problem.

SUMMARY OF THE INVENTION

The present invention has been achieved in view of the above-described problems. An object of the present invention is to realize a moisture detector of closed case type according to a heat capacity method and having a relatively simple constitution so as to stably maintain a condition in which aerobic bacteria are easily activated in a garbage disposer, for example.

In order to solve the above-described problems, a moisture detector according to a first aspect of the present invention comprises: a first temperature sensor for sensing temperature of a detection target; a second temperature sensor for sensing the temperature of the detection target; heating means for heating the second temperature sensor; and processing means for obtaining information relating to moisture percentage in the detection target on the basis of a signal outputted from the first temperature sensor and a signal outputted from the second temperature sensor heated by the heating means.

Further, a moisture detector according to a second aspect of the present invention comprises: a temperature sensor for sensing temperature of a detection target; heating means for heating the temperature sensor; and processing means for determining whether a rainfall starts or not on the basis of a signal outputted from the temperature sensor not heated by the heating means and a signal outputted from the temperature sensor heated by the heating means.

According to the first aspect of the present invention, a closed case type moisture detector according to a heat capacity method is realized with a relatively simple constitution by obtaining information relating to moisture percentage on the basis of temperature information sensed by two kinds of temperature sensors in two kinds of heat conditions.

Further, according to the second aspect of the present invention, a closed case type moisture detector according to a heat capacity method is realized with a relatively simple constitution by determining whether a rainfall starts or not on the basis of temperature information sensed by a single temperature sensor in two kinds of heat conditions.

DESCRIPTION OF THE PREFERRED EMBODIMENTS

Hereinafter, embodiments of the present invention will be described in detail by referring to the drawings.

Figure 1:
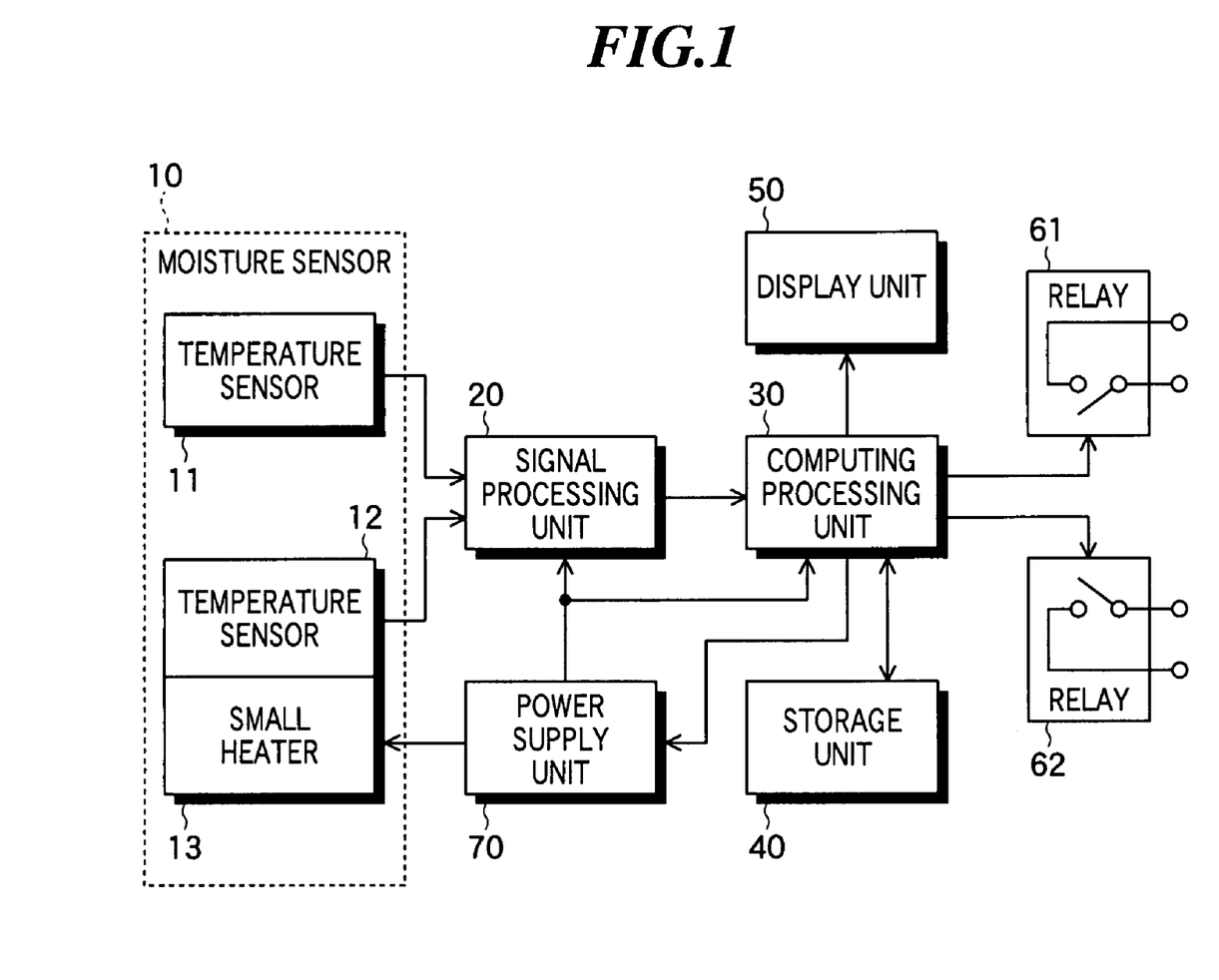
FIG. 1 is a block diagram showing the constitution of a moisture detector according to a first embodiment of the present invention.

FIG. 1 is a block diagram showing the constitution of a moisture detector according to a first embodiment of the present invention. The moisture detector according to this embodiment is suitable for use in a garbage disposer, for example.

As shown in FIG. 1, this moisture detector has a moisture sensor 10 for outputting two kinds of detection signals, a signal processing unit 20 for performing signal processing such as amplification and A/D conversion on the two kinds of detection signals outputted from the moisture sensor 10, a computing processing unit 30 for obtaining information relating to moisture percentage in a detection target on the basis of digital signals outputted from the signal processing unit 20, a storage unit 40 for storing the information required for obtaining the information relating to moisture percentage, a display unit 50 for displaying various kinds of values in accordance with a display signal outputted from the computing processing unit 30, two relays 61 and 62 for opening and closing respective circuits on the basis of control signals outputted from the computing processing unit 30, and a power supply unit 70 for supplying power supply voltages to the respective units. Here, the signal processing unit 20, the computing processing unit 30, and the storage unit 40 may be integrated as a single small module.

Figure 2:
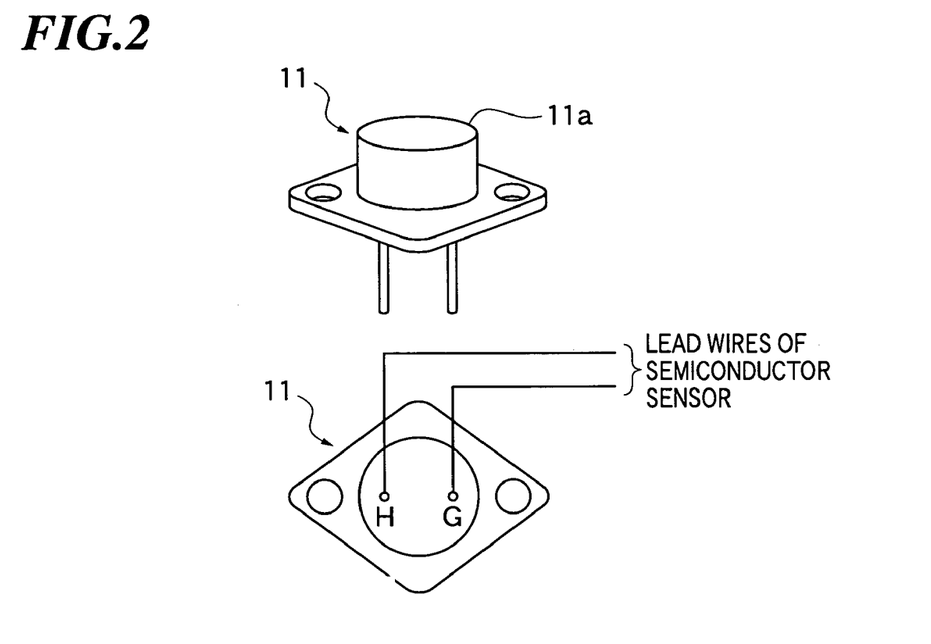
FIG. 2 is a diagram showing the overview of a temperature sensor 11 as shown in FIG. 1.
Figure 3:
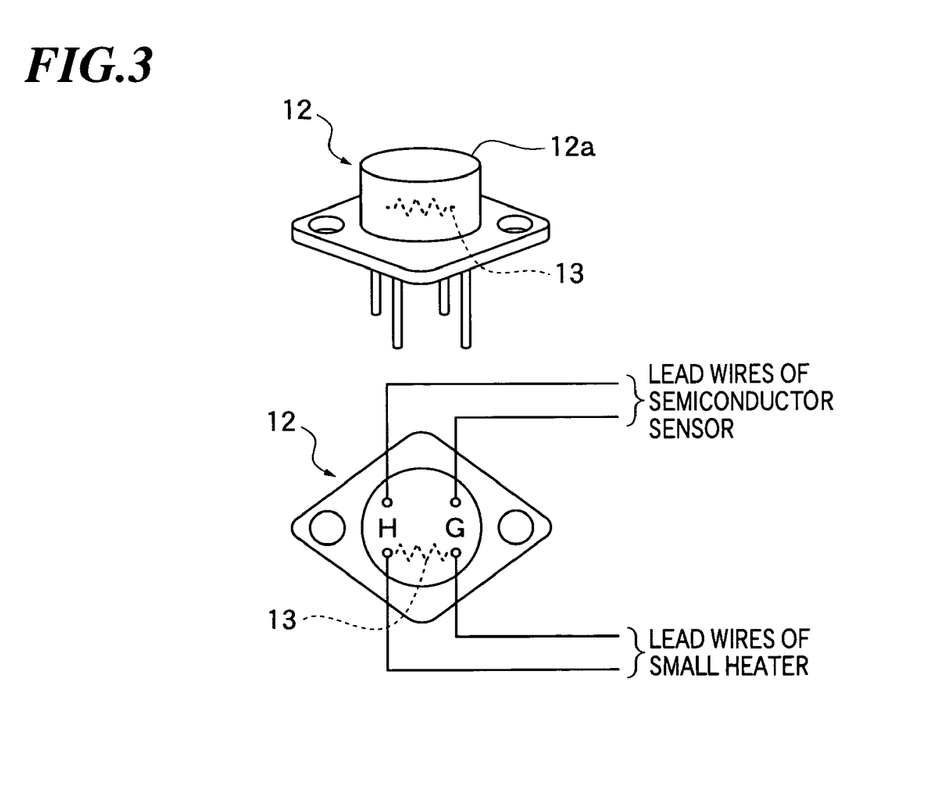
FIG. 3 is a diagram showing the overview of a temperature sensor 12 as shown in FIG. 1.

The moisture sensor 10 is a heat capacity type sensor and includes a first temperature sensor 11 and a second temperature sensor 12 for sensing the temperature of a detection target and outputting heat sensing signals and a small heater 13 as heating means for heating the temperature sensor 12. As shown in FIG. 2, the first temperature sensor 11 is formed by enclosing a semiconductor sensor such as a diode or thermistor within a closed case 11a made of a material having good corrosion resistance, aberration resistance, and impact resistance such as aluminum and stainless steel. To a hot (H) terminal and a ground (G) terminal of the semiconductor sensor, two lead wires are connected. Further, as shown in FIG. 3, the second temperature sensor 12 is formed by enclosing a semiconductor sensor such as a diode or thermistor within a closed case 12a that is the same as the closed case 11a, and, within the closed case 12a, the small heater 13 is also enclosed. To a hot (H) terminal and a ground (G) terminal of the semiconductor sensor, two lead wires are connected, and to a hot (H) terminal and a ground (G) terminal of the small heater 13, two lead wires are also connected.

When the moisture percentage detection is performed, the first and second temperature sensors 11 and 12 are disposed so as to be in direct contact with the detection target, and current is supplied to the small heater 13 so as to make the heat generation thereof into a predetermined value. In the state in which the small heater 13 generates heat, the first temperature sensor 11 senses the temperature of the detection target and the second temperature sensor 12 heated by the small heater 13 senses the temperature of the detection target. Thus, the first and second temperature sensors 11 and 12 output two kinds of temperature sensing signals.

Figure 4:
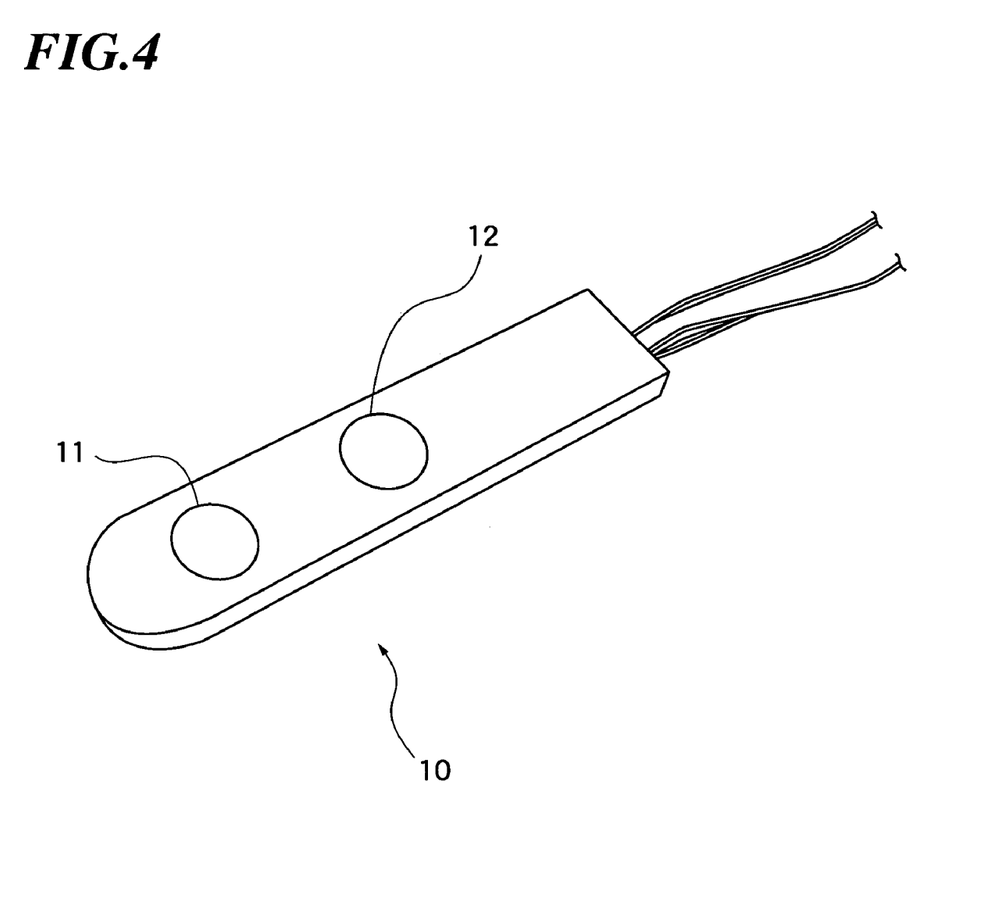
FIG. 4 is a diagram showing the overview of a moisture sensor 10 as shown in FIG. 1.

Further, in the case where the moisture detector according to the embodiment is used for detecting the moisture percentage in the soil in a horticultural facility such as a plastic house etc., it is desirable to use a moisture sensor 10 formed by integrating a temperature sensor 11 and a temperature sensor 12 with a small sensor built in as shown in FIG. 4 by digging it into the soil at the depth of 5 cm to 10 cm with the sensor surface facing upside.

Referring to FIG. 1 again, the two kinds of temperature sensing signals outputted from the first and second temperature sensors 11 and 12 are inputted to the signal processing unit 20. The signal processing unit 20 amplifies these sensing signals, A/D converting the amplified sensing signals, and further performing signal processing such as nonlinear correction thereon so as to generate a first digital signal representing a first temperature sensed by the first temperature sensor 11 and a second digital signal representing a second temperature sensed by the second temperature sensor 12. The first and second digital signals are supplied to the computing processing unit 30.

The computing processing unit 30 is constituted by a CPU, for example. To the computing processing unit 30, the storage unit 40 for storing software (control program) for allowing the CPU to perform operation is connected. As the storage unit 40, for example, a semiconductor memory such as EEPROM is used, for example. Further, in the storage unit 40, according to the kind of the detection target, the information relating to the moisture percentage in the detection target is stored in correspondence with the relationships between the first temperature sensed by the first temperature sensor 11 and the second temperature sensed by the second temperature sensor 12 heated by the small heater 13.

The computing processing unit 30 performs computation on the basis of the first digital signal representing the first temperature sensed by the first temperature sensor 11 and the second digital signal representing the second temperature sensed by the second temperature sensor 12 heated by the small heater 13 and making reference to a value stored in the storage unit 40 on the basis of the value obtained by the computation so as to obtain information relating to the moisture percentage in the detection target.

For example, in the storage unit 40, according to the kind of garbage as the detection target, a moisture percentage table representing the relationship between (i) the difference value between the first temperature sensed by the first temperature sensor 11 and the second temperature sensed by the second temperature sensor 12 and (ii) the moisture percentage in the garbage. The value in the moisture percentage table has been obtained in advance on the basis of experiments, etc. The computing processing unit 30 obtains the difference value between the first temperature represented by the first digital signal and the second temperature represented by the second digital signal and obtains the moisture percentage in the garbage by making reference to the value stored in the storage unit 40 on the basis of the difference value.

Owing to the heat generation by the small heater 13, the second temperature sensed by the second temperature sensor 12 becomes higher than the first temperature sensed by the first temperature sensor 11. Further, assuming that the heat generation from the small heater 13 is constant, the curves of temperature rise are different in correspondence with the moisture percentage contained in the detection target material. That is, the higher the moisture percentage in garbage becomes, the larger the heat capacity of the garbage becomes and even when the second temperature sensor 12 is heated by the small heater 13, a large amount of heat is drawn by the garbage and the difference between temperatures sensed by the temperature sensors 11 and 12 becomes small. On the other hand, the lower the moisture percentage in garbage becomes, the smaller the heat capacity of the garbage becomes and when the second temperature sensor 12 is heated by the small heater 13, an amount of heat drawn by the garbage is small and the difference between temperatures sensed by the temperature sensors 11 and 12 becomes large.

Figure 5:
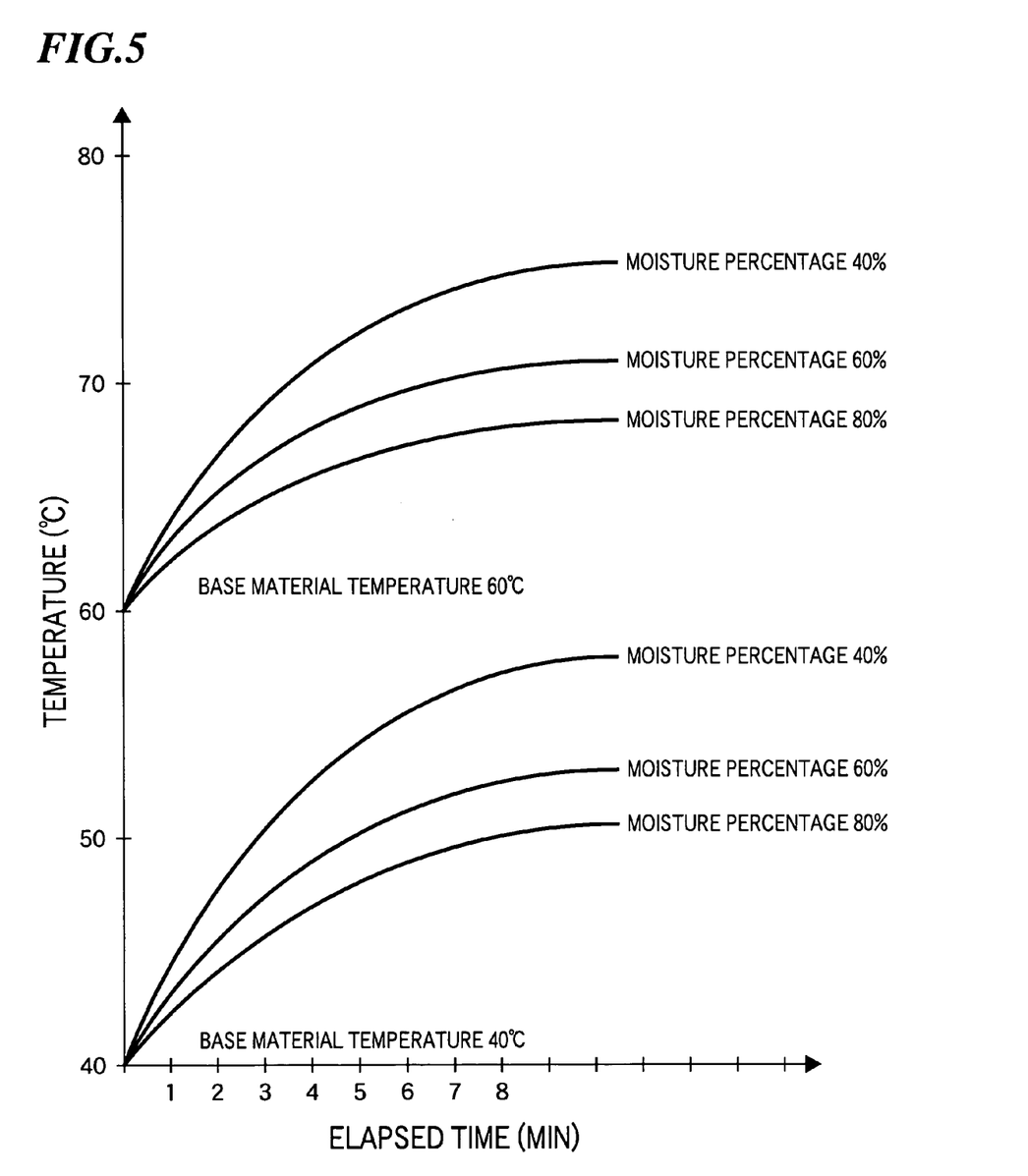
FIG. 5 is a graph showing an example of temperature rise to elapsed time in the moisture detector according to the first embodiment of the present invention.

FIG. 5 shows an example of temperature rise to elapsed time. In FIG. 5, regarding the cases where the initial value of the base material temperature of the first temperature sensor 11 is 40° C. and 60° C., changes in the temperature measured by the second temperature sensor 12 under the environment of the moisture percentages of 40%, 60%, and 80% are shown. Utilizing such relationships, the moisture percentage in the detection target can be detected on the basis of the temperatures sensed by the temperature sensors 11 and 12. By maintaining the moisture percentage in the garbage at 50% to 60% on the basis of the moisture percentage detected by the moisture detector, the condition in which the aerobic bacteria are activated easily is created stably. Further, in the temperature sensors 11 and 12, since the semiconductor sensors are enclosed in the closed cases respectively, unlike the electric resistance type moisture sensor, the sensors can operate satisfactorily even in the garbage.

Referring to FIG. 1 again, the display unit 50 displays the measured first temperature, second temperature, the difference of these or the detected moisture percentage in accordance with the display signal outputted from the computing processing unit 30. Further, the lower limit value and the upper limit value of the moisture percentage have been stored in advance in the storage unit 40, the computing processing unit 30 activates the first control signal when the detected moisture percentage is lower than the lower limit value, and activates the second control signal when the detected moisture percentage is upper than the upper limit value. The relay 61 closes the circuit in accordance with the first control signal when the moisture percentage is lower than the lower limit value, and the relay 62 closes the circuit in accordance with the second control signal when the moisture percentage is higher than the upper limit value. Thereby, a moisture controller can be constituted which operates a moisturizing device connected to the relay 61 when the moisture percentage becomes lower and/or operates a drying device connected to the relay 62 when the moisture percentage becomes higher so as to keep the moisture percentage in the detection target at substantially constant value.

Next, the second embodiment of the present invention will be described. A moisture detector according to this embodiment is suitable for use as a rainfall detector, for example.

When a rainfall starts during large-scale watering in a vast farm, the watering is continued even during the rainfall and wasted. Further, a rainfall starts during watering lawns or planters by using a sprinkler or the like in a housing district of an urban area, the watering is wasted similarly. Furthermore, when laundry is dried in the sun in a general household, or, in a working site for drying agricultural products or fish catches, a closed case type rainfall detector would be convenient.

Figure 6:
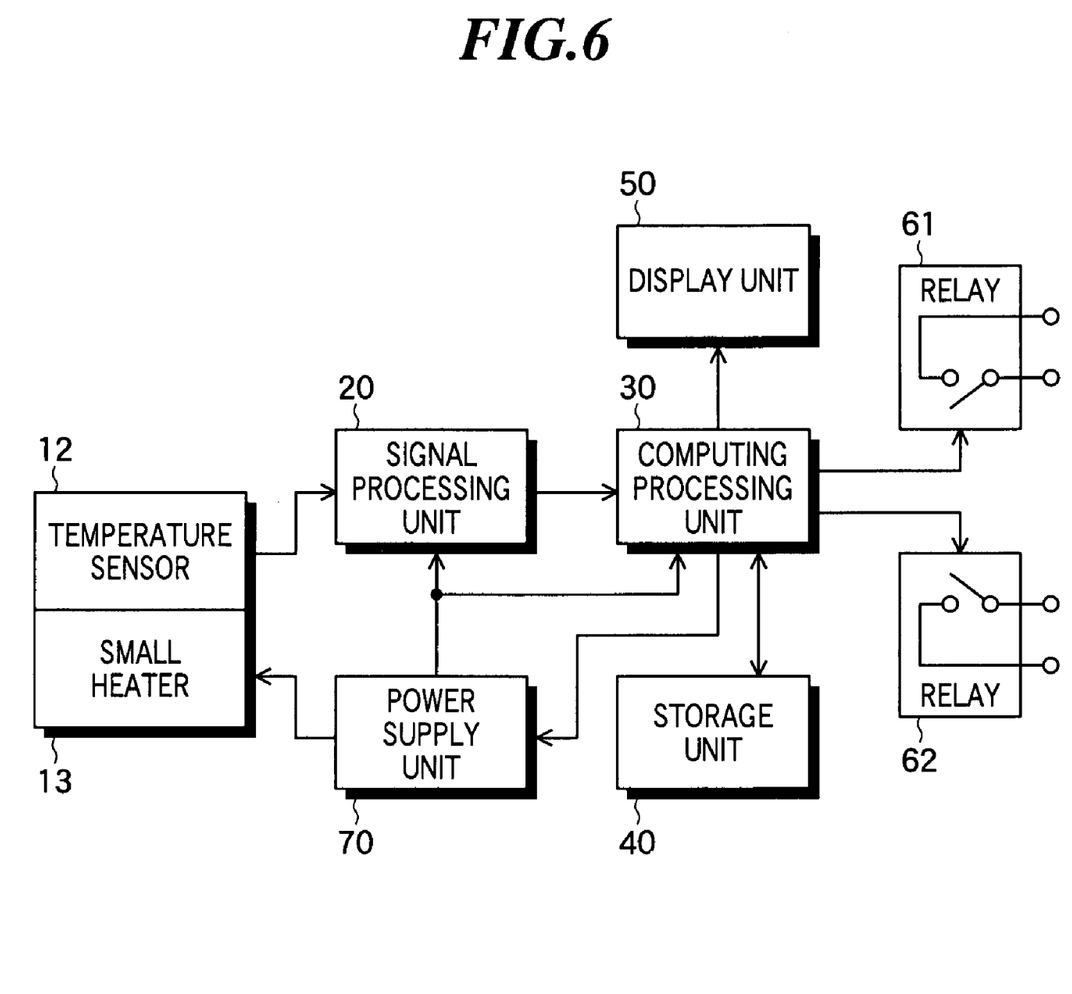
FIG. 6 is a block diagram showing the constitution of a moisture detector according to a second embodiment of the present invention.

FIG. 6 is a block diagram showing the constitution of a moisture detector according to the second embodiment. In this moisture detector, the first temperature sensor 11 is omitted from the moisture detector according to the first embodiment as shown in FIG. 1, and accordingly, the operation in the computing processing unit 30 is different from the first embodiment. In the first embodiment, the first temperature sensor 11 senses the reference temperature and thereby the measurement accuracy is improved, however, in the case of using the moisture detector as a rainfall detector, since only the temperature change from the dry condition in fine weather into the condition when one or several drops of rain hit the temperature sensor is needed to be detected, there is no need to detect the reference temperature at all times.

Figure 7:
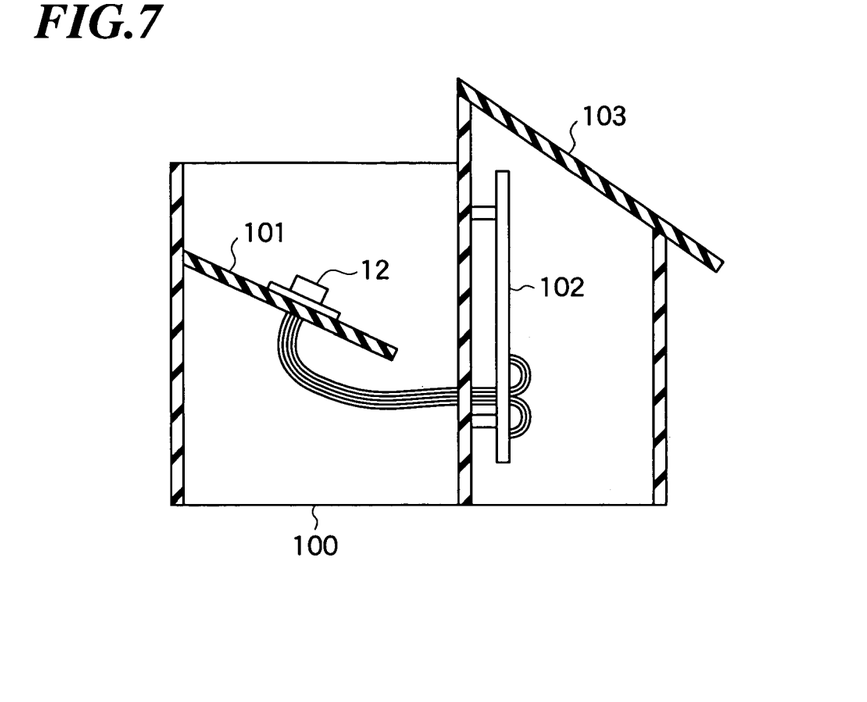
FIG. 7 is a sectional view showing the structure of the moisture detector according to the second embodiment of the present invention.

FIG. 7 is a sectional view showing the structure of the moisture detector according to the second embodiment of the present invention. In a housing 100, a baseboard 101 on which a temperature sensor 12 with a small heater built in is mounted slantingly. This part of the housing 100 is in the tubular form and opens above and below the temperature sensor 12. On the other hand, by a wall surrounding the temperature sensor 12, the influence on the temperature measurement by winds is prevented. Further, because of the slantingly mounted baseboard 101, dirt and dust accumulated on the baseboard 101 are washed off by rain or the like.

The lead wire from the temperature sensor 12 is connected to a printed wiring board 102 disposed in the next chamber. For preventing the printed wiring board 102 from getting wet, a roof 103 is provided on the upper part of the chamber in which the printed wiring board 102 is disposed. On the printed wiring board 102, a signal processing unit 20, a computing processing unit 30, a storage unit 40, a display unit 50, two relays 61 and 62, and a power supply unit 70 as shown in FIG. 6, and other required circuits are mounted.

The operation of the moisture detector according to this embodiment will be described. First, in a condition in which current is not supplied to the small heater 13, the heat sensing signal outputted from the temperature sensor 12 is A/D converted in the signal processing unit 20, and a digital signal representing a first temperature is obtained. This digital signal is supplied to the computing processing unit 30. Then, the computing processing unit 30 controls the power supply unit 70 to supply current to the small heater 13 so as to make the heat generation of the small heater 13 into a predetermined value. After that, the heat sensing signal outputted from the temperature sensor 12 is A/D converted in the signal processing unit 20, and a digital signal representing a second temperature is obtained. This digital signal is supplied to the computing processing unit 30.

Figure 8:
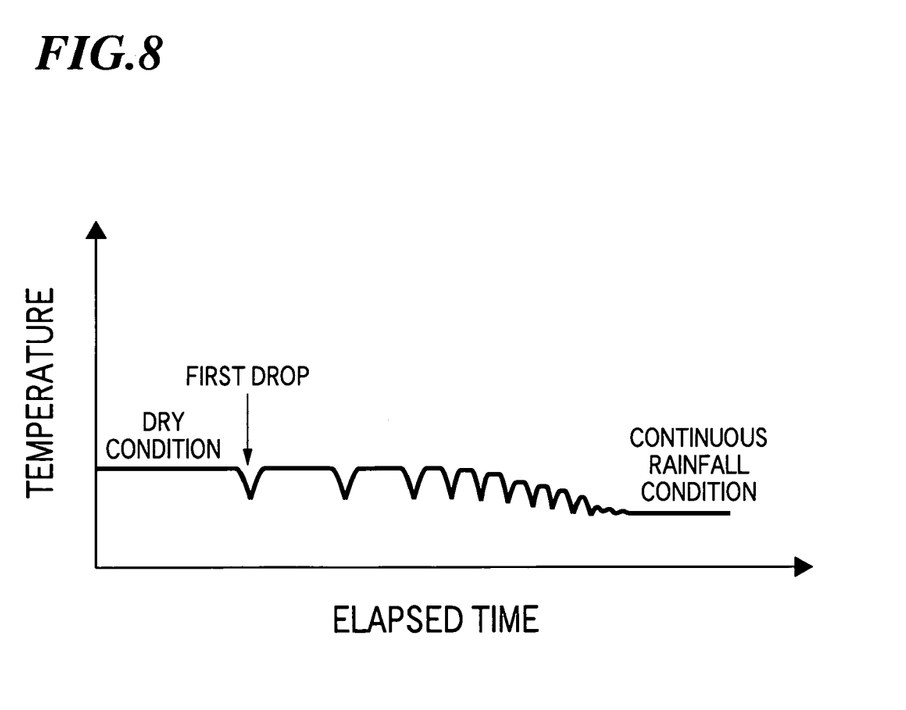
FIG. 8 is a graph showing temperature change measured by the moisture detector according to the second embodiment of the present invention.

FIG. 8 shows the temperature change measured by the moisture detector according to this embodiment. In a dry condition, the measured second temperature is higher than the first temperature before heating. However, when the first drop of rain hits the temperature sensor 12, the second temperature drops temporarily. After that, the second temperature drops at each time when a rain drop hits the temperature sensor 12, and, in the continuous rainfall condition, the second temperature remains low. Therefore, the computing processing unit 30 can determine whether a rainfall starts or not by detecting the change in the second temperature. For the detection of the temperature change, for example, a threshold value set to a value between the first temperature and the second temperature is used. The computing processing unit 30 compares the measured second temperature with the threshold value, and determines whether a rainfall starts or not on the basis of, for example, a number of times when the second temperature becomes lower than the threshold value in a predetermined period. Further, the computing processing unit 30 may stop the current supply when a predetermined period is elapsed after the current is supplied to the small heater 13 and reset the measurement conditions, and then, start the measurement again.

The computing processing unit 30 controls the relays 61 and 62 to close the circuit of the relay 61 and open the circuit of the relay 62 in a dry condition, and, when a rainfall is detected, controls the relays 61 and 62 to open the circuit of the relay 61 and close the circuit of the relay 62. The relay 61 is used for supplying a power supply voltage to the sprinkler, for example. When the circuit of the relay 61 is opened at the start of a rainfall, the sprinkler supplied with the power supply voltage via the relay 61 is stopped. On the other hand, the relay 62 is used for giving a rainfall alarm, for example. When the circuit of the relay 62 is closed at the start of a rainfall, an alarm device supplied with the power supply voltage via the relay 62 is started to operate.

The moisture detector according to this embodiment can also be used as a snowfall detector or an icing detector. When the temperature becomes equal to or less than 0° C., rain often changes into snow or ice. Accordingly, in the case where the first temperature measured in the initial condition is nearly equal to or less than 0° C., the computing processing unit 30 can determine whether snow fall or icing starts or not on the basis of, for example, a number of times when the second temperature becomes lower than the threshold value in a predetermined period.

The invention claimed is:

1. A moisture detector comprising:
   a first temperature sensor formed by enclosing a first semiconductor sensor within a first closed case, for sensing a temperature of a detection target;
   a second temperature sensor formed by enclosing a second semiconductor sensor within a second closed case, for sensing the temperature of said detection target;
   heating means enclosed in said second closed case, for generating constant heat to heat said second temperature sensor;
   storage means for storing information relating to moisture percentage in said detection target in correspondence with a difference value between a value based on a temperature to be sensed by said first temperature sensor and a value based on a temperature to be sensed by said second temperature sensor when heated by said heating means; and
   processing means for obtaining a difference value between a first value based on a signal output by said first temperature sensor and a second value based on a signal output by said second temperature sensor heated by said heating means so as to obtain information relating to moisture percentage in said detection target from said storage means on the basis of the difference value.

2. A moisture detector according to claim 1, wherein said processing means includes:
   signal processing means for amplifying the signals respectively output by said first and second temperature sensors and A/D converting the amplified signals to obtain the first and second values, respectively; and
   computing processing means for obtaining the difference value between the first value and the second value to refer to a value stored in said storage means on the basis of the difference value.

3. A moisture detector according to claim 1, wherein:
   said storage means further stores an upper limit value and a lower limit value relating to the moisture percentage in said detection target; and
   said processing means activates a first control signal in the case where the obtained moisture percentage is larger than the upper limit value and activates a second control signal in the case where the obtained moisture percentage is smaller than the lower limit value.

4. A moisture detector according to claim 1, wherein each of said first and second temperature sensors includes one of a diode and a thermistor.

5. A moisture detector according to claim 1, wherein said processing means outputs a display signal to be used for displaying the obtained moisture percentage on a display unit.

* * * * *